(12) United States Patent
Sims

(10) Patent No.: US 11,490,953 B2
(45) Date of Patent: Nov. 8, 2022

(54) ELECTROSURGICAL INSTRUMENT AND PASSIVELY COOLED JAW MEMBERS THEREOF

(71) Applicant: COVIDIEN LP, Mansfield, MA (US)

(72) Inventor: Grant T. Sims, Boulder, CO (US)

(73) Assignee: Covidien LP, Mansfield, MA (US)

( * ) Notice: Subject to any disclaimer, the term of this patent is extended or adjusted under 35 U.S.C. 154(b) by 773 days.

(21) Appl. No.: 16/148,017

(22) Filed: Oct. 1, 2018

(65) Prior Publication Data

US 2020/0100833 A1    Apr. 2, 2020

(51) Int. Cl.
  *A61B 18/14*    (2006.01)
  *A61B 18/00*    (2006.01)

(52) U.S. Cl.
  CPC ...... *A61B 18/1445* (2013.01); *A61B 18/1402* (2013.01); *A61B 2018/0063* (2013.01); *A61B 2018/00077* (2013.01); *A61B 2018/00095* (2013.01); *A61B 2018/00601* (2013.01); *A61B 2018/1452* (2013.01)

(58) Field of Classification Search
  CPC ............ A61B 18/1445; A61B 18/1402; A61B 18/1442; A61B 2018/00077; A61B 2018/00095; A61B 2018/00601; A61B 2018/0063; A61B 2018/1452
  See application file for complete search history.

(56) References Cited

U.S. PATENT DOCUMENTS

| | | | |
|---|---|---|---|
| 7,147,638 B2 | 12/2006 | Chapman et al. | |
| 7,169,146 B2 | 1/2007 | Truckai et al. | |
| 8,075,555 B2 | 12/2011 | Truckai et al. | |
| 8,920,461 B2 | 12/2014 | Unger et al. | |
| 2006/0217709 A1* | 9/2006 | Couture | A61B 18/1442 606/51 |
| 2009/0163916 A1* | 6/2009 | Paul | A61B 18/1492 606/41 |
| 2011/0306968 A1* | 12/2011 | Beckman | A61B 18/1482 606/41 |
| 2012/0083786 A1* | 4/2012 | Artale | A61B 34/76 606/51 |
| 2015/0112195 A1* | 4/2015 | Berger | A61B 18/1492 600/433 |
| 2017/0065325 A1* | 3/2017 | Takei | A61B 18/085 |
| 2017/0231651 A1* | 8/2017 | Dinger | A61B 18/1445 604/20 |

FOREIGN PATENT DOCUMENTS

| | | |
|---|---|---|
| EP | 0246350 A1 | 11/1987 |
| WO | 2012116957 A1 | 9/2012 |

* cited by examiner

*Primary Examiner* — Michael F Peffley
*Assistant Examiner* — Bo Ouyang

(57) ABSTRACT

An electrosurgical instrument includes an elongated first shaft fabricated from thermally-conductive plastic material, an elongated second shaft, and opposing first and second jaw members each having a proximal end portion coupled to a distal end portion of the respective first and second shafts. One or both of the jaw members has a jaw frame and an electrically-conductive tissue sealing structure disposed over the jaw frame. The first shaft has a heat sink disposed therein configured to dissipate heat from the tissue sealing structure toward the thermally-conductive plastic material.

20 Claims, 3 Drawing Sheets

ELECTROSURGICAL INSTRUMENT AND PASSIVELY COOLED JAW MEMBERS THEREOF

BACKGROUND

1. Technical Field

The present disclosure relates to electrosurgical instruments. More particularly, the present disclosure relates to an open surgical forceps having jaw members that effectively dissipate heat.

2. Discussion of Related Art

Electrosurgical instruments have become widely used by surgeons. Electrosurgery involves the application of electrical energy and/or electromagnetic energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue. In monopolar electrosurgery, a patient return electrode, also called a grounding pad, bovie pad, neutral electrode or patient plate, is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, both the active electrode and return electrode functions are performed at the site of surgery. Bipolar electrosurgical devices include two electrodes of opposite polarity that are located in proximity to one another for the application of current between their surfaces. Bipolar electrosurgical current travels from one electrode, through the intervening tissue to the other electrode to complete the electrical circuit, thereby eliminating the need for a remotely-located current return. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to achieve hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of an end effector and that are both electrically coupled to an electrosurgical generator. In bipolar forceps, the end-effector assembly generally includes opposing jaw assemblies pivotably mounted with respect to one another. In a bipolar configuration, only the tissue grasped between the jaw assemblies is included in the electrical circuit.

SUMMARY

According to an aspect of the present disclosure, an electrosurgical instrument is provided and includes an elongated first shaft fabricated from a thermally-conductive plastic material and having a heat sink disposed therein, an elongated second shaft, and opposing first and second jaw members each having a proximal end portion coupled to a distal end portion of the respective first and second shafts. At least one of the first or second members is movable relative to the other from a first position in which the jaw members are disposed in spaced relation relative to one another to at least a second position closer to one another in which the jaw members cooperate to grasp tissue therebetween. The first jaw member includes a jaw frame and an electrically-conductive tissue sealing structure coupled to the jaw frame. The heat sink is configured to dissipate heat from the tissue sealing structure toward the first shaft.

In aspects, the heat sink may include a mesh of interwoven metal fibers.

In some aspects, the mesh of interwoven metal fibers may be fabricated from aluminum and/or copper.

In further aspects, the mesh of interwoven metal fibers may be received in a cavity defined in the first shaft.

In other aspects, the mesh of interwoven metal fibers may extend a majority of a length of the first shaft.

In aspects, the second shaft may be fabricated from thermally-conductive plastic material and may have a heat sink disposed therein.

In some aspects, the first jaw member may include a thermally-conductive material disposed between the jaw frame and the tissue sealing structure. The thermally-conductive material may be configured to draw heat from the tissue sealing structure and dissipate heat toward the first shaft via the heat sink.

In further aspects, the thermally-conductive material may have a proximal end portion coupled to a distal end portion of the heat sink.

In other aspects, the first jaw member may further include an insulator between the thermally-conductive material and the tissue sealing structure.

In aspects, the insulator may have a central portion defining a longitudinally-extending knife slot. The central portion of the insulator may be received in a longitudinally-extending slot defined in the thermally-conductive material.

In some aspects, the first shaft may have a plurality of fins attached to an outer surface thereof. The fins may be fabricated from the thermally-conductive plastic material.

In accordance with another aspect of the present disclosure, an electrosurgical instrument is provided and includes an elongated first shaft fabricated from a thermally-conductive plastic material, an elongated second shaft, and opposing first and second jaw members each having a proximal end portion coupled to a distal end portion of the respective first and second shafts. At least one of the first or second members is movable relative to the other from a first position in which the jaw members are disposed in spaced relation relative to one another to at least a second position closer to one another in which the jaw members cooperate to grasp tissue therebetween. The first jaw member includes a jaw frame, an electrically-conductive tissue sealing structure coupled to the jaw frame, and a thermally-conductive material disposed between the jaw frame and the tissue sealing structure. The thermally-conductive material is configured to draw heat from the tissue sealing structure and dissipate heat toward the first shaft.

In some aspects, the first jaw member may further include an insulator disposed over the thermally-conductive material. The tissue sealing structure may be disposed over the insulator and isolated from the thermally-conductive material by the insulator.

In further aspects, the insulator may have a central portion defining a longitudinally-extending knife slot. The central portion of the insulator may be received in a longitudinally-extending slot defined in the thermally-conductive material.

In other aspects, the thermally-conductive material may be fabricated from a metal and the first shaft may have a mesh of interwoven metal fibers disposed therein coupled to the thermally-conductive material.

In aspects, the thermally-conductive material may have a proximal end portion coupled to a distal end portion of the mesh of interwoven metal fibers.

In some aspects, the mesh of interwoven metal fibers may be received in a cavity defined in the first shaft.

In further aspects, the mesh of interwoven metal fibers may extend a majority of a length of the first shaft.

In other aspects, the second shaft may be fabricated from thermally-conductive plastic material and may have a heat sink disposed therein.

In aspects, the second jaw member may include a jaw frame, an electrically-conductive tissue sealing structure coupled to the jaw frame, and a thermally-conductive material disposed between the jaw frame and the tissue sealing structure. The thermally-conductive material may be configured to draw heat from the tissue sealing structure of the second jaw member and dissipate the heat toward the second shaft via the heat sink in the second shaft.

BRIEF DESCRIPTION OF THE DRAWINGS

Objects and features of the presently-disclosed electrosurgical instruments adapted for tissue dissection and coagulation will become apparent to those of ordinary skill in the art when descriptions of various embodiments thereof are read with reference to the accompanying drawings, of which.

DETAILED DESCRIPTION

Figure 1:
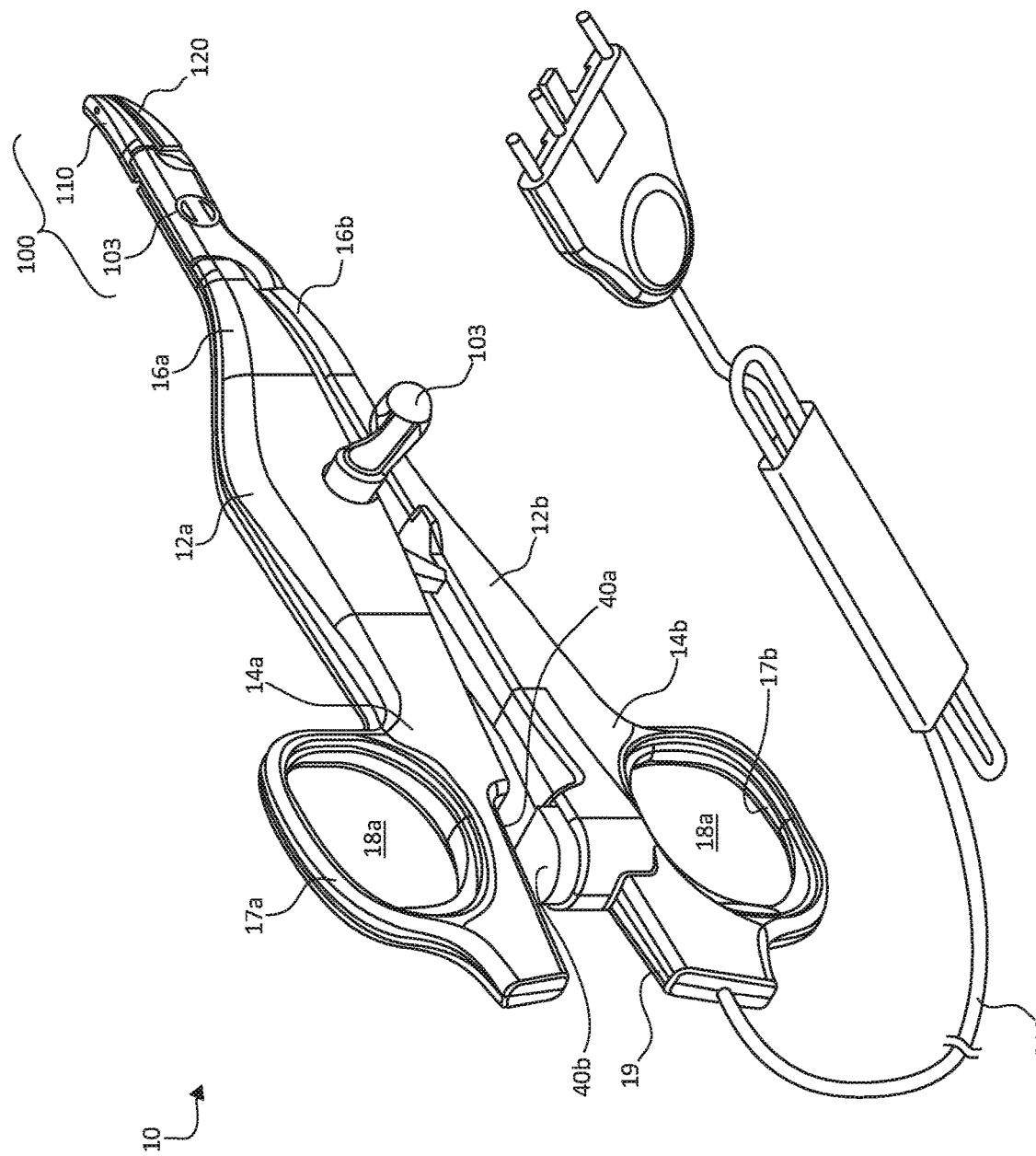
FIG. 1 is a side, perspective view of a forceps according to an aspect of the present disclosure.

Hereinafter, embodiments of electrosurgical instrument of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the instrument, or component thereof, closer to the user, and the term "distal" refers to that portion of the instrument, or component thereof, farther from the user.

As will be described in detail herein, provided is an electrosurgical instrument that includes a pair of elongated shafts pivotable relative to one another, and a pair of jaw members coupled to the respective shafts. The shafts are fabricated from a thermally-conductive plastic material and have a mesh of metal fibers disposed therein. The jaw members may each have a thermally-conductive plate disposed therein and electrically isolated from a tissue sealing plate of the respective jaw members. The thermally-conductive plates are thermally coupled at their proximal ends to a distal end of the corresponding metal meshes in the shafts. During use, heat generated in the tissue sealing plates is transferred to the thermally-conductive plates in the jaw members, which transfers the heat to the metal mesh, and ultimately to the thermally-conductive plastic material that makes up the shafts.

Referring now to FIG. 1, an electrosurgical instrument, such as for example, an open forceps 10 contemplated for use in connection with traditional open surgical procedures is shown. For the purposes herein, either an open instrument, e.g., forceps 10, or an endoscopic instrument (not shown) may be utilized in accordance with the present disclosure. Different electrical and mechanical connections and considerations apply to each particular type of instrument; however, the novel aspects with respect to the open forceps and its operating characteristics remain generally consistent with respect to both the open and endoscopic configurations.

The forceps 10 includes elongated first and second shafts 12a and 12b, each having a proximal end portion 14a and 14b, and a distal end portion 16a and 16b, respectively. Forceps 10 further includes an end effector assembly 100 attached to the distal end portions 16a and 16b of the shafts 12a and 12b, respectively. The end effector assembly 100 includes a pair of opposing jaw members 110 and 120 that are pivotably connected about a pivot 103. Each shaft 12a and 12b includes a handle 17a and 17b disposed at the proximal end portion 14a and 14b thereof. Each handle 17a and 17b defines a finger hole 18a and 18b therethrough for receiving a finger of the user. As can be appreciated, the finger holes 18a and 18b facilitate movement of the shafts 12a and 12b relative to one another between a spaced-apart position and an approximated position, which, in turn, pivots the jaw members 110 and 120 from an open position, in which the jaw members 110 and 120 are disposed in spaced-apart relation to one another, to a closed position, in which the jaw members 110 and 120 cooperate to grasp tissue therebetween. The jaw members 110, 120 of the end effector assembly 100 may be engaged to the first and second shafts 12b, 12a, respectively, via welding, or any other suitable manufacturing process.

One of the shafts, e.g., shaft 12b, includes a proximal shaft connector 19 that is designed to connect the forceps 10 to a source of electrosurgical energy such as an electrosurgical generator (not shown). The proximal shaft connector 19 secures an electrosurgical cable 210 to the forceps 10 such that the user may selectively apply electrosurgical energy to electrically-conductive tissue sealing structures 112 and 122 (see FIG. 2) of the jaw members 110 and 120, respectively. More specifically, the cable 210 includes a wire (or wires) (not shown) extending therethrough that has sufficient length to extend through one of the shaft members, e.g., shaft member 12b, in order to provide electrical energy to at least one of the sealing structures 112, 122 of the jaw members 110, 120, respectively, of the end effector assembly 100. Alternatively, the forceps 10 may be configured as a battery-powered instrument.

The second shaft 12b includes an activation switch 40b disposed at the proximal end portion 14b thereof and extends from second shaft 12b toward the first shaft 12a. A corresponding surface 40a (FIG. 2) is defined along the first shaft 12a toward the proximal end portion 14a thereof and is configured to actuate the activation switch 40b. More specifically, upon approximation of the first and second shafts 12a, 12b, e.g., when the jaw members 110, 120 are moved to the closed position, the activation switch 40b is moved into contact with, or in close proximity of the surface 40a. Upon further approximation of the first and second shafts 12a, 12b, e.g., upon application of a pre-determined closure force to the jaw members 110, 120, the activation switch 40b is advanced further into the surface 40a to depress the activation switch 40b. The activation switch 40b controls the supply of electrosurgical energy to the jaw members 110, 120 such that, upon depression of the activation switch 40b, electrosurgical energy is supplied to the sealing structure 112 and/or the sealing structure 122 of the jaw members 110, 120, respectively, to seal tissue grasped therebetween. Other activation switches are also contemplated, e.g., finger switch, toggle switch, foot switch, etc.

Figure 2:
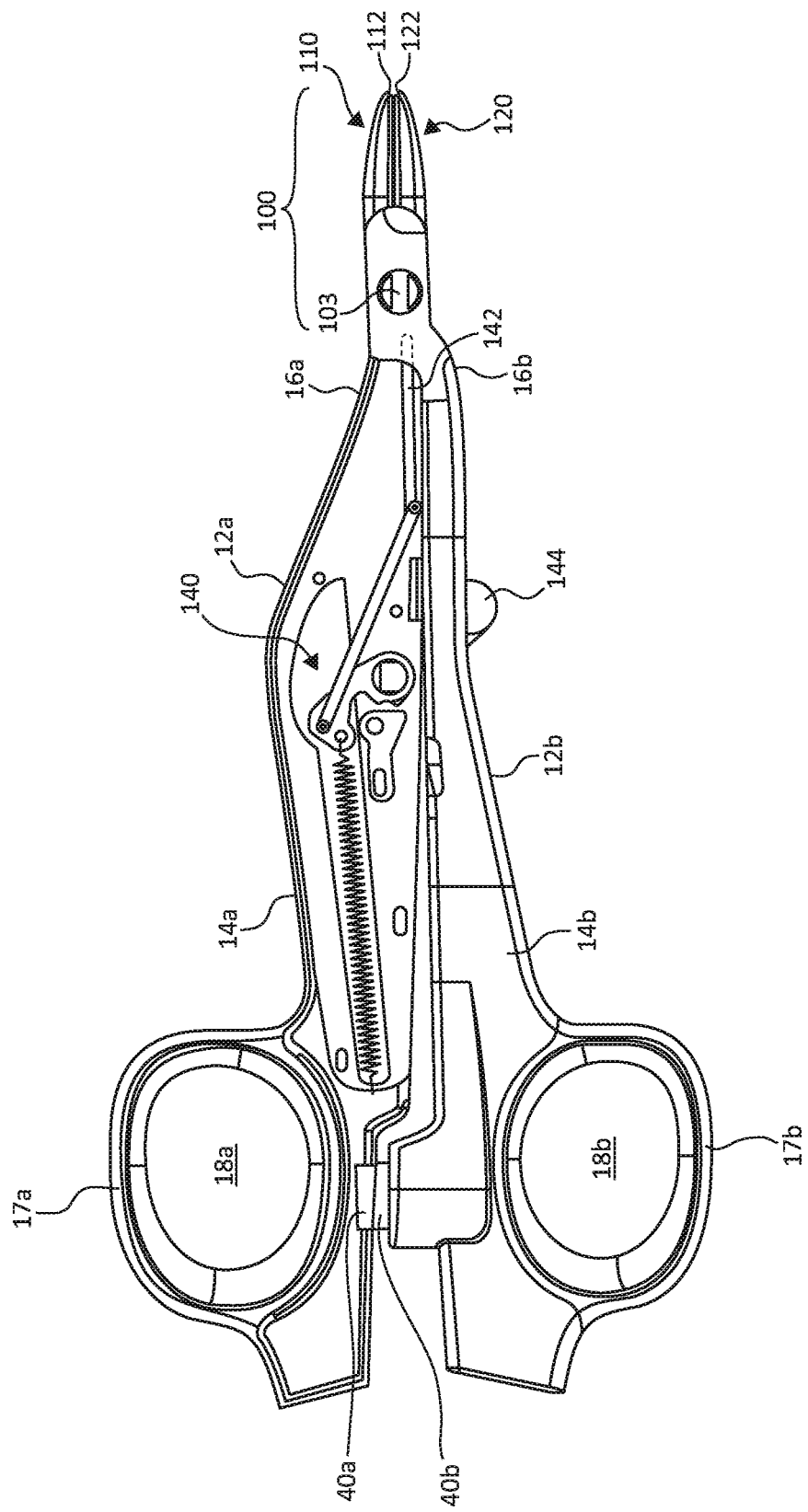
FIG. 2 is side view of the forceps of FIG. 1 with a portion of one of a pair of shafts removed to show the internal components thereof.

With reference to FIG. 2, in conjunction with FIG. 1, the forceps 10 may further include a knife assembly 140 disposed within one of the first and second shafts, e.g., the first shaft 12a, and a knife channel 115 (FIG. 5A) defined within one or both of the jaw members 110, 120 to permit reciprocation of a knife 142 of the knife assembly 140 therethrough. The knife assembly 140 includes a rotatable trigger 144 that is rotatable about a pivot for advancing the knife 142 from a retracted position within the first shaft 12a (as shown FIG. 2), to an extended position (not explicitly shown), in which the knife 144 extends into the knife channel 115 to divide tissue grasped between the jaw members 110, 120. In other words, axial rotation of the trigger 144 effects longitudinal translation of the knife 142. Other trigger assemblies are also contemplated.

Figure 3:
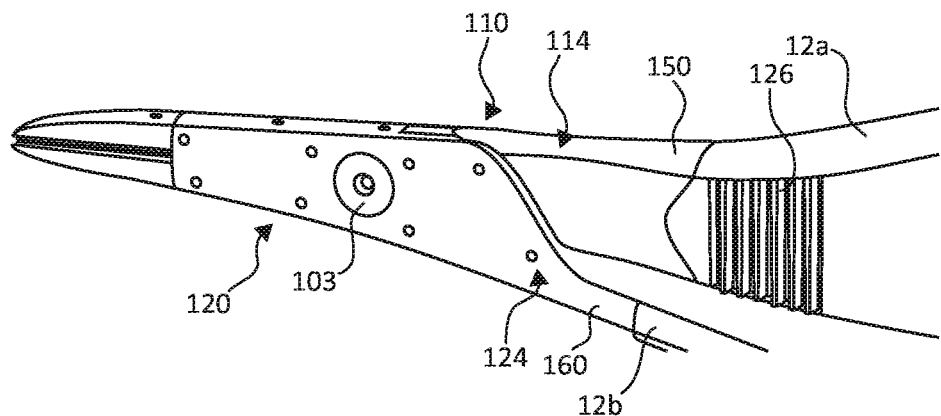
FIG. 3 is an enlarged side, perspective view of a distal end portion of the forceps of FIG. 1, illustrating first and second shafts having an end effector assembly coupled thereto.
Figure 4:
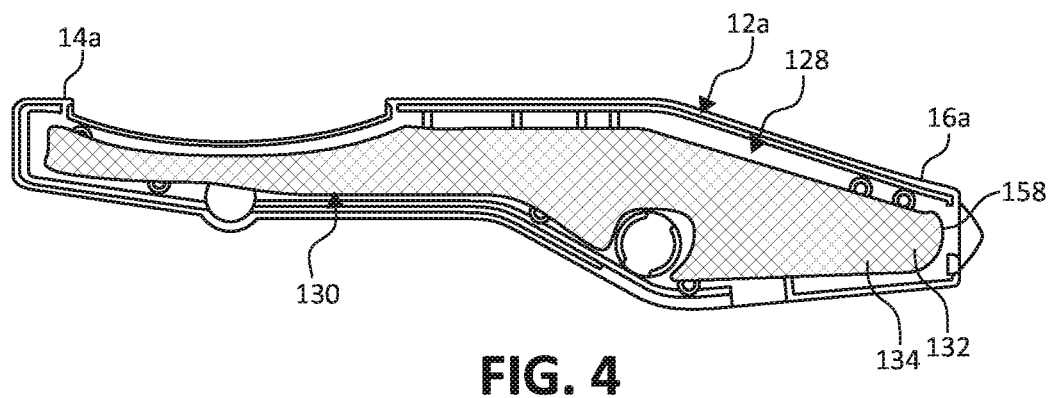
FIG. 4 is a longitudinal, cross-sectional view of one of the shafts of FIG. 3, illustrating a heat sink disposed therein.

With reference to FIGS. 3 and 4, the first and second shafts 12a, 12b are each fabricated from a plastic material that is thermally-conductive while being electrically-nonconductive. For example, the shafts 12a, 12b may be fabricated from THERMA-TECH™ thermally conductive compounds by PolyOne®. In other embodiments, the first and second shafts 12a, 12b may be fabricated from a material that is thermally-conductive while being electrically-conductive. The plastic material making up the first and second shafts 12a, 12b has both a high convection rate and a high thermal conductivity rate to enable heat to be distributed evenly throughout and away from a heat source, such as, for example, the seal structures 112, 122 (FIG. 2) of the respective first and second jaw members 110, 120.

The first and second shafts 12a, 12b each further include a plurality of fins 126 attached to an outer surface thereof. In embodiments, the fins 126 may be monolithically formed with the outer surface of the shafts 12a, 12b or connected to the outer surface of the shafts 12a, 12b. The fins 126 may be parallel with and spaced from one another to define elongated slits between adjacent fins 126. The fins 126 are fabricated from a thermally-conductive plastic material; however, in embodiments, the fins 126 may be fabricated from a different type of material than the shafts 12a, 12b, such as, for example, a metal. In other embodiments, the fins 126 may be fabricated from the thermally-conductive plastic material, whereas the remainder of the first shaft 12a may be fabricated from any suitable material, including metals and plastics.

The first shaft 12a defines a cavity 128 having a heat sink 130 disposed therein. The heat sink 130 may be suspended within the cavity 128 of the first shaft 12a or in contact with inner surfaces of the shaft 12a. In some aspects, the first shaft 12a may define a plurality of holes, vents, slots, or the like (not shown) in an outer surface thereof in communication with the cavity 128. The second shaft 12b includes a similar heat sink as the first shaft 12a, and will therefore not be further described herein. The heat sink 130 extends along a majority of the length of the shaft 12a, and in embodiments, an entire length of the shaft 12a. The heat sink 130 includes a mesh of interwoven metal fibers 132 defining a plurality of apertures 134 throughout. The metal fibers 132 may be any suitably conductive non-metal or metal, such as, for example, copper and/or aluminum. In embodiments, the heat sink 130 may be a solid block of conductive material.

With continued reference to FIGS. 3-5B, each jaw member 110, 120 of the end effector assembly 100 includes a jaw frame 114, 124 having a proximal end portion 150, 160 engagable with one another to permit pivoting of the jaw members 110, 120 relative to one another between the open position and the closed position upon movement of the first and second shafts 12a, 12b relative to one another between the spaced-apart and approximated positions. The proximal end portions 150, 160 of the jaw members 110, 120 also connect the jaw members 110, 120 to the distal end portions 16a, 16b of the respective first and second shafts 12b, 12a thereof, e.g., via welding or any other suitable fastening engagement. The jaw frames 114, 124 are fabricated from a metal, such as, for example, stainless steel; however, other materials are contemplated.

The first jaw member 110 further includes a thermally-conductive material 136 disposed on the jaw frame 114, an insulator 138 disposed on the thermally-conductive material 136, the seal plate 112 disposed on the insulator 138, and an insulative outer jaw housing 152 at least partially enclosing the jaw frame 114, the thermally-conductive material 136, and the insulator 138. The second jaw member 120 includes similar elements that correspond to the first jaw member 110. Therefore, the components of the second jaw member 120 will not be further described herein.

The thermally-conductive material 136 of the first jaw member 110 may be in the form of a plate having first and second longitudinal sections 136a, 136b (FIG. 5B) that extend along respective first and second opposed lateral sides of the first jaw member 110 and a curved distal portion 136b extending around a curved distal tip of the first jaw member 110. The thermally-conductive material 136 may be fabricated from a metal, such as, for example, copper, steel, and/or aluminum. Other types of metals are contemplated. The thermally-conductive material 136 may define a centrally-located, longitudinally-extending channel 154 to allow for the passage of the knife 142 (FIG. 2) of the knife assembly 140. The thermally-conductive material 136 has a proximal end portion 156 coupled (e.g., welded or in abutment) with a distal end portion 158 of the heat sink 130 in the first shaft 12a. As such, heat absorbed by the thermally-conductive material 136 of the first jaw member 110 is freely dissipated into the heat sink 130 in the first shaft 12a. In some aspects, heat sink paste or thermal pads may be provided under the seal plates 112 or at any suitable location of forceps 10.

The insulator 138 of the first jaw member 110 is disposed atop an upper surface of the thermally-conductive material 136 and under the first sealing structure 112. The insulator 138 is configured to electrically isolate the tissue sealing structure 112 from the remaining components of the respective jaw member 110, e.g., the thermally-conductive material 136. The insulator 138 has a central portion 162 defining a longitudinally-extending knife slot 164 dimensioned for the slidable passage of the knife 142 (FIG. 2). The central portion 162 of the insulator 138 is received in the slot 154 defined in the thermally-conductive material 136. The outer jaw housing 152 may be over-molded about the jaw frame 114, the thermally-conductive material 136, and the insulator 138 to engage the components of the jaw member 110 to one another. Other manufacturing methods are also contemplated.

Figure 5A:
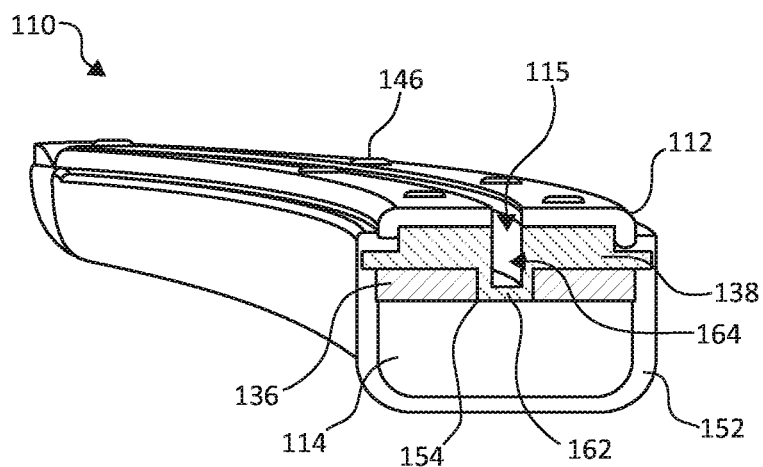
FIG. 5A is a side, cross-sectional view of a jaw member of the end effector assembly of FIG. 3.
Figure 5B:
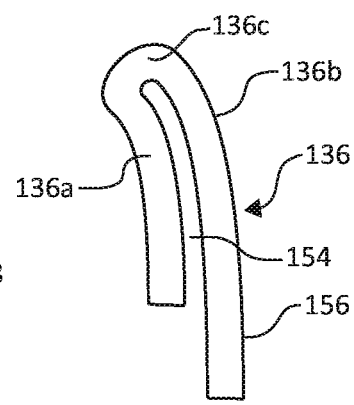
FIG. 5B is a top view of a thermally-conductive plate of the jaw member of FIG. 5A.

As shown in FIG. 5A, at least one of the jaw members, e.g., the first jaw member 110, includes at least one stop member 146 disposed on the inner facing surfaces of the electrically conductive sealing structure 112. Alternatively or in addition, the stop member(s) 146 may be disposed adjacent to the electrically conductive sealing structure 112 or proximate the pivot 103. The stop member(s) 146 facilitates gripping and manipulation of tissue and act to define a gap between opposing jaw members 110 and 120 during sealing and cutting of tissue. In some embodiments, the stop member(s) 146 maintains a gap distance between opposing jaw members 110 and 120 within a range of about 0.001 inches (0.03 millimeters) to about 0.006 inches (0.015 millimeters).

In operation, electrosurgical energy is transferred to the first tissue sealing structure 112 of the first jaw member 110 to treat tissue disposed between the first and second jaw members 110, 120. Heat generated in the tissue sealing structure 112 is absorbed by the thermally-conductive material 136 disposed underneath, which then transfers the heat to the jaw frame 114. Since the proximal end portion 156 of the thermally-conductive material 136 of the jaw member 110 is thermally coupled to the distal end portion 158 of the heat sink 130 in the first shaft 12a, heat in the thermally-conductive material 136 is also transferred to the heat sink 130. Due to the first shaft 12a being fabricated from the thermally-conductive plastic material, the heat in the heat sink 130 is readily absorbed by the first shaft 12a and dissipated to the environment via the fins 126 in the first shaft 12a and/or the entire outer surface of the first shaft 12a.

For a more detailed description of various features of an exemplary open vessel sealer, reference may be made to U.S. Pat. No. 8,920,461, filed on Mar. 1, 2012, the entire contents of which are incorporated by reference herein.

The above-described end-effector embodiments may be used in connection with sealing plates and support bases of jaw assemblies of varied geometries, e.g., lengths and curvatures, such that variously-configured jaw assemblies may be fabricated and assembled into various end-effector configurations.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical instrument, comprising:
    an elongated first shaft having a proximal end portion and a distal end portion each fabricated from a thermally-conductive plastic material, the elongated first shaft having a heat sink disposed therein;
    an elongated second shaft having a proximal end portion and a distal end portion; and
    opposing first and second jaw members each having a proximal end portion coupled to the distal end portion of the respective first and second shafts, at least one of the first or second members is movable relative to the other from a first position in which the jaw members are disposed in spaced relation relative to one another to at least a second position closer to one another in which the jaw members cooperate to grasp tissue therebetween, the first jaw member including:
    a jaw frame; and
    an electrically-conductive tissue sealing structure coupled to the jaw frame, wherein the heat sink is configured to dissipate heat from the electrically-conductive tissue sealing structure toward the first shaft.

2. The electrosurgical instrument according to claim 1, wherein the heat sink includes a mesh of interwoven metal fibers.

3. The electrosurgical instrument according to claim 2, wherein the mesh of interwoven metal fibers is fabricated from at least one of aluminum or copper.

4. The electrosurgical instrument according to claim 2, wherein the mesh of interwoven metal fibers is received in a cavity defined in the first shaft.

5. The electrosurgical instrument according to claim 2, wherein the mesh of interwoven metal fibers extends a majority of a length of the first shaft.

6. The electrosurgical instrument according to claim 1, wherein the second shaft is fabricated from a thermally-conductive plastic material and has a heat sink disposed therein.

7. The electrosurgical instrument according to claim 1, wherein the first jaw member includes a thermally-conductive material disposed between the jaw frame and the electrically-conductive tissue sealing structure, the thermally-conductive material configured to draw heat from the electrically-conductive tissue sealing structure and dissipate heat toward the first shaft via the heat sink.

8. The electro surgical instrument according to claim 7, wherein the thermally-conductive material has a proximal end portion coupled to a distal end portion of the heat sink.

9. The electro surgical instrument according to claim 7, wherein the first jaw member further includes an insulator disposed between the thermally-conductive material and the electrically-conductive tissue sealing structure.

10. The electrosurgical instrument according to claim 9, wherein the insulator has a central portion defining a longitudinally-extending knife slot, the central portion of the insulator received in a longitudinally-extending slot defined in the thermally-conductive material.

11. The electrosurgical instrument according to claim 1, wherein the first shaft has a plurality of fins attached to an outer surface thereof, the plurality of fins fabricated from the thermally-conductive plastic material.

12. The electrosurgical instrument according to claim 1, wherein the second shaft is fabricated from a thermally-conductive plastic material and has a heat sink disposed therein.

13. The electrosurgical instrument according to claim 12, wherein the second jaw member includes:
    a jaw frame;
    an electrically-conductive tissue sealing structure coupled to the jaw frame of the second jaw member; and
    a thermally-conductive material disposed between the jaw frame of the second jaw member and the electrically-conductive tissue sealing structure of the second jaw member, wherein the thermally-conductive material is configured to draw heat from the electrically-conductive tissue sealing structure of the second jaw member and dissipate the heat toward the second shaft via the heat sink in the second shaft.

14. An electrosurgical instrument, comprising:
    an elongated first shaft fabricated from a thermally-conductive plastic material, the elongated first shaft having a proximal end portion defining a handle, the handle being fabricated from the thermally-conductive plastic material;

an elongated second shaft; and opposing first and second jaw members each having a proximal end portion coupled to a distal end portion of the respective first and second shafts, at least one of the first or second members is movable relative to the other from a first position in which the jaw members are disposed in spaced relation relative to one another to at least a second position closer to one another in which the jaw members cooperate to grasp tissue therebetween, the first jaw member including:

a jaw frame;

an electrically-conductive tissue sealing structure coupled to the jaw frame; and a thermally-conductive material disposed between the jaw frame and the electrically-conductive tissue sealing structure, wherein the thermally-conductive material is configured to draw heat from the electrically-conductive tissue sealing structure and dissipate heat toward the first shaft.

15. The electrosurgical instrument according to claim 14, wherein the first jaw member further includes an insulator disposed between the thermally-conductive material and the electrically-conductive tissue sealing structure.

16. The electrosurgical instrument according to claim 15, wherein the insulator has a central portion defining a longitudinally-extending knife slot, the central portion of the insulator received in a longitudinally-extending slot defined in the thermally-conductive material.

17. The electrosurgical instrument according to claim 14, wherein the thermally-conductive material is fabricated from a metal and the first shaft has a mesh of interwoven metal fibers disposed therein coupled to the thermally-conductive material.

18. The electrosurgical instrument according to claim 17, wherein the thermally-conductive material has a proximal end portion coupled to a distal end portion of the mesh of interwoven metal fibers.

19. The electrosurgical instrument according to claim 17, wherein the mesh of interwoven metal fibers is received in a cavity defined in the first shaft.

20. The electrosurgical instrument according to claim 17, wherein the mesh of interwoven metal fibers extends a majority of a length of the first shaft.

\* \* \* \* \*